United States Patent
Rapoport

(10) Patent No.: US 10,606,090 B2
(45) Date of Patent: Mar. 31, 2020

(54) MULTI-BEAM SPLITTING USING SPATIAL BEAM SEPARATION

(71) Applicant: Novartis AG, Basel (CH)

(72) Inventor: Tobias Jura Rapoport, Berlin (DE)

(73) Assignee: ALCON INC. (CH)

( * ) Notice: Subject to any disclaimer, the term of this patent is extended or adjusted under 35 U.S.C. 154(b) by 6 days.

(21) Appl. No.: 16/213,266

(22) Filed: Dec. 7, 2018

(65) Prior Publication Data

US 2019/0179159 A1 Jun. 13, 2019

Related U.S. Application Data

(60) Provisional application No. 62/597,652, filed on Dec. 12, 2017.

(51) Int. Cl.
| | |
|---|---|
| *G02B 27/14* | (2006.01) |
| *A61B 3/13* | (2006.01) |
| *A61B 3/14* | (2006.01) |
| *A61F 9/007* | (2006.01) |
| *G06T 11/60* | (2006.01) |
| *G02B 21/36* | (2006.01) |
| *G02B 21/00* | (2006.01) |
| *A61F 9/008* | (2006.01) |
| *A61B 90/00* | (2016.01) |

(52) U.S. Cl.
CPC .......... *G02B 27/144* (2013.01); *A61B 3/13* (2013.01); *A61B 3/14* (2013.01); *A61F 9/007* (2013.01); *G02B 21/0012* (2013.01); *G02B 21/368* (2013.01); *G06T 11/60* (2013.01); *A61B 2090/373* (2016.02); *A61B 2505/05* (2013.01); *A61F 9/00736* (2013.01); *A61F 2009/0087* (2013.01); *A61F 2009/00874* (2013.01); *A61F 2009/00887* (2013.01); *G06T 2210/41* (2013.01)

(58) Field of Classification Search
CPC .............. H04N 2201/0246; A61B 3/13; A61B 1/00195; A61B 3/0041; G02B 27/10–16; G02B 21/0012; A61F 2009/0087
USPC .................................................. 359/618–640
See application file for complete search history.

(56) References Cited

U.S. PATENT DOCUMENTS

| | | | |
|---|---|---|---|
| 2015/0077705 A1 | 3/2015 | Artsyukhovich | |
| 2016/0357003 A1* | 12/2016 | Hauger | G02B 21/0012 |

FOREIGN PATENT DOCUMENTS

| | | |
|---|---|---|
| WO | WO2017029561 A1 | 2/2017 |
| WO | WO2017093851 A1 | 6/2017 |
| WO | WO2017189283 A1 | 11/2017 |

* cited by examiner

*Primary Examiner* — Christopher K Peterson
(74) *Attorney, Agent, or Firm* — Joseph Weatherbee, Esq.

(57) ABSTRACT

A multi-beam splitter enables superimposing overlay content onto an optical field of view of a microscope using a compact and flexible design that is cost-effective for many applications. The multi-beam splitter also enables capturing of the optical field of view without the overlay content.

30 Claims, 3 Drawing Sheets

MULTI-BEAM SPLITTING USING SPATIAL BEAM SEPARATION

BACKGROUND

Field of the Disclosure

The present disclosure relates to optical components, and more specifically, to multi-beam splitting using spatial beam separation.

Description of the Related Art

In ophthalmology, eye surgery, or ophthalmic surgery, saves and improves the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make an enormous difference in the patient's vision after the surgery.

Ophthalmic surgery is performed on the eye and accessory visual structures, and may encompass vitreoretinal surgery and cataract surgery, among others. Specifically, vitreoretinal surgery encompasses various delicate procedures involving internal portions of the eye, such as the vitreous humor and the retina. Different vitreoretinal surgical procedures are used, sometimes with lasers, to improve visual sensory performance in the treatment of many eye diseases, including epimacular membranes, diabetic retinopathy, vitreous hemorrhage, macular hole, detached retina, and complications of cataract surgery, among others. During vitreoretinal surgery, an ophthalmologist typically uses a surgical microscope to view the fundus through the cornea, while surgical instruments that penetrate the sclera may be introduced to perform any of a variety of different procedures. The surgical microscope provides imaging and optionally illumination of the fundus during ophthalmic surgery. The patient typically lies supine under the surgical microscope during surgery and a speculum is used to keep the eye exposed. Depending on a type of optical system used, the ophthalmologist has a given field of view of the fundus, which may vary from a narrow field of view to a wide field of view that can extend to peripheral regions of the fundus.

During cataract surgery, which is performed on the anterior portion of the eye that is externally visible, a diseased lens may be removed from the lenticular bag and replaced with an artificial lens, such as an intraocular lens (IOL). During cataract surgery, the cornea and the iris may be viewed using a surgical microscope to enable implanation of the artificial lens through an incision in the cornea, as well as to align and properly seat the new artificial lens.

The surgical microscope used in ophthalmic surgery may also be enabled for image-based surgery assistance, in which additional image content may be overlaid onto the field of view that a surgeon may view, such as at an ocular of the surgical microscope. Such overlay content may also be used in other types of general applications of microscopy. For the purposes of generating and displaying such overlay content, a compact and flexible coaxial alignment of beams providing flexibility of light throughput is desired.

SUMMARY

In one aspect, a first multi-beam splitter is disclosed. The first multi-beam splitter may include a beam splitter configured to receive a first beam at a first surface and a second beam at a second surface opposite the first surface. In the first multi-beam splitter, the beam splitter may transmit a first partial beam of the first beam and may reflect a second partial beam of the first beam, while the beam splitter may transmit a third partial beam of the second beam and may reflects a fourth partial beam of the second beam. The first multi-beam splitter may further include a spot filter comprising an opaque spot having a first radius, the opaque spot arranged coaxially to the second beam to filter the second beam at the second surface, and an aperture filter comprising a transparent aperture having a second radius, the transparent aperture arranged coaxially to the second partial beam to transmit the second partial beam from the first surface. In the first multi-beam splitter, the opaque spot of the spot filter may be coaxially aligned with the transparent aperture of the aperture filter and the first radius is equal to or greater than the second radius, while the third partial beam may be blocked at the aperture filter.

In any of the disclosed embodiments of the first multi-beam splitter, the first beam may be received along a first optical axis and the second beam may be received along a second optical axis that is perpendicular to the first optical axis.

In any of the disclosed embodiments of the first multi-beam splitter, the beam splitter may be oriented 45 degrees with respect to the first optical axis and the second optical axis.

In any of the disclosed embodiments of the first multi-beam splitter, the first partial beam and the fourth partial beam may leave the first multi-beam splitter along the first optical axis.

In any of the disclosed embodiments of the first multi-beam splitter, the second partial beam may leave the first multi-beam splitter along the second optical axis.

In another aspect, an first optical system is disclosed including a first source generating a first beam, a second source generating a second beam, and a multi-beam splitter enabled to receive the first beam and the second beam. In the first optical system, the multi-beam splitter may further include a beam splitter configured to receive the first beam at a first surface and the second beam at a second surface opposite the first surface. In the first optical system, the beam splitter may transmit a first partial beam of the first beam and may reflect a second partial beam of the first beam, while the beam splitter may transmit a third partial beam of the second beam and may reflect a fourth partial beam of the second beam. In the first optical system, the multi-beam splitter may further include a spot filter comprising an opaque spot having a first radius, the opaque spot arranged coaxially to the second beam to filter the second beam at the second surface, and an aperture filter comprising a transparent aperture having a second radius, the transparent aperture arranged coaxially to the second partial beam to transmit the second partial beam from the first surface. In the first optical system, the opaque spot of the spot filter may be coaxially aligned with the transparent aperture of the aperture filter and the first radius may be equal to or greater than the second radius, while the third partial beam may be blocked at the aperture filter.

In any of the disclosed embodiments of the first optical system, the first beam may be received along a first optical axis and the second beam may be received along a second optical axis that is perpendicular to the first optical axis.

In any of the disclosed embodiments of the first optical system, the beam splitter may be oriented 45 degrees with respect to the first optical axis and the second optical axis.

In any of the disclosed embodiments of the first optical system, the first partial beam and the fourth partial beam may leave the multi-beam splitter along the first optical axis.

In any of the disclosed embodiments of the first optical system, the second partial beam may leave the multi-beam splitter along the second optical axis.

In any of the disclosed embodiments, the first optical system may further include an optical sensor receiving the second partial beam from the aperture filter.

In any of the disclosed embodiments of the first optical system, the second source may be a display and the second beam may include overlay content generated by the display, while the first optical system may further include an ocular receiving the first partial beam and the fourth partial beam. In the first optical system, the overlay content may be overlaid onto an image of the first source for viewing at the ocular.

In any of the disclosed embodiments of the first optical system, the first source may be an eye of a patient subject to ophthalmic surgery.

In any of the disclosed embodiments of the first optical system, the overlay content may be generated using an output from the optical sensor.

In any of the disclosed embodiments of the first optical system, the optical sensor may be a camera.

In yet another aspect, a second multi-beam splitter is disclosed. The second multi-beam splitter may include a beam splitter configured to receive a first beam at a first surface and a second beam at a second surface opposite the first surface. In the second multi-beam splitter, the beam splitter may transmit a first partial beam of the first beam and may reflect a second partial beam of the first beam, while the beam splitter may transmit a third partial beam of the second beam and may reflects a fourth partial beam of the second beam. The second multi-beam splitter may further include an aperture filter comprising an opaque field and a transparent aperture having a second radius, the transparent aperture arranged coaxially to the second beam to filter the second beam at the second surface, and a spot filter comprising a transparent field and an opaque spot having a first radius, the opaque spot arranged coaxially to the second partial beam to transmit the second partial beam from the first surface. In the second multi-beam splitter, the opaque spot of the spot filter may be coaxially aligned with the transparent aperture of the aperture filter and the second radius is equal to or greater than the first radius, while the third partial beam may be blocked at the spot filter.

In any of the disclosed embodiments of the second multi-beam splitter, the first beam may be received along a first optical axis and the second beam may be received along a second optical axis that is perpendicular to the first optical axis.

In any of the disclosed embodiments of the second multi-beam splitter, the beam splitter may be oriented 45 degrees with respect to the first optical axis and the second optical axis.

In any of the disclosed embodiments of the second multi-beam splitter, the first partial beam and the fourth partial beam may leave the second multi-beam splitter along the first optical axis.

In any of the disclosed embodiments of the second multi-beam splitter, the second partial beam may leave the second multi-beam splitter along the second optical axis.

In still a further aspect, an second optical system is disclosed including a first source generating a first beam, a second source generating a second beam, and a multi-beam splitter enabled to receive the first beam and the second beam. In the second optical system, the multi-beam splitter may further include a beam splitter configured to receive the first beam at a first surface and the second beam at a second surface opposite the first surface. In the second optical system, the beam splitter may transmit a first partial beam of the first beam and may reflect a second partial beam of the first beam, while the beam splitter may transmit a third partial beam of the second beam and may reflect a fourth partial beam of the second beam. In the second optical system, the multi-beam splitter may further include an aperture filter comprising an opaque field and a transparent aperture having a second radius, the transparent aperture arranged coaxially to the second beam to filter the second beam at the second surface, and a spot filter comprising a transparent field and an opaque spot having a first radius, the opaque spot arranged coaxially to the second partial beam to transmit the second partial beam from the first surface. In the second optical system, the opaque spot of the spot filter may be coaxially aligned with the transparent aperture of the aperture filter and the second radius may be equal to or greater than the first radius, while the third partial beam may be blocked at the spot filter.

In any of the disclosed embodiments of the second optical system, the first beam may be received along a first optical axis and the second beam may be received along a second optical axis that is perpendicular to the first optical axis.

In any of the disclosed embodiments of the second optical system, the beam splitter may be oriented 45 degrees with respect to the first optical axis and the second optical axis.

In any of the disclosed embodiments of the second optical system, the first partial beam and the fourth partial beam may leave the multi-beam splitter along the first optical axis.

In any of the disclosed embodiments of the second optical system, the second partial beam may leave the multi-beam splitter along the second optical axis.

In any of the disclosed embodiments, the second optical system may further include an optical sensor receiving the second partial beam from the spot filter.

In any of the disclosed embodiments of the second optical system, the second source may be a display and the second beam may include overlay content generated by the display, while the second optical system may further include an ocular receiving the first partial beam and the fourth partial beam. In the second optical system, the overlay content may be overlaid onto an image of the first source for viewing at the ocular.

In any of the disclosed embodiments of the second optical system, the first source may be an eye of a patient subject to ophthalmic surgery.

In any of the disclosed embodiments of the second optical system, the overlay content may be generated using an output from the optical sensor.

In any of the disclosed embodiments of the second optical system, the optical sensor may be a camera.

BRIEF DESCRIPTION OF THE DRAWINGS

For a more complete understanding of the present disclosure, reference is now made to the following description, taken in conjunction with the accompanying drawings, in which.

DETAILED DESCRIPTION

Figure 1:
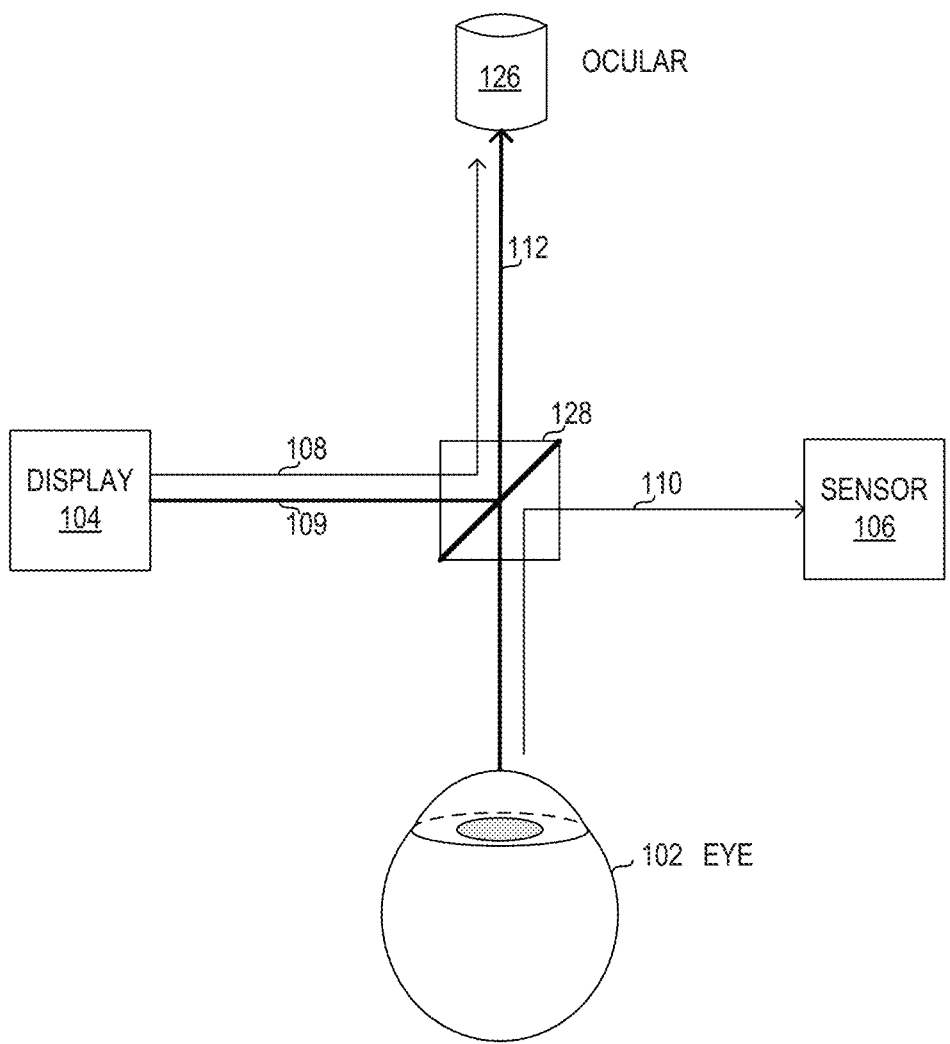
FIG. 1 is a depiction of optical elements of a multi-beam splitting instrument.

In the following description, details are set forth by way of example to facilitate discussion of the disclosed subject matter. It should be apparent to a person of ordinary skill in the field, however, that the disclosed implementations are exemplary and not exhaustive of all possible implementations.

As used herein, a hyphenated form of a reference numeral refers to a specific instance of an element and the un-hyphenated form of the reference numeral refers to the collective element. Thus, for example, device '12-1' refers to an instance of a device class, which may be referred to collectively as devices '12' and any one of which may be referred to generically as a device '12'.

As noted above, during ophthalmic surgery, such as vitreoretinal surgery or cataract surgery, a surgeon may view a portion of an eye of a patient using a surgical microscope. For example, during vitreoretinal surgery the fundus may be viewed in conjunction with an ophthalmic lens for viewing through the cornea, such as a contact or non-contact lens. During cataract surgery, the anterior portion of the eye may be viewed through the cornea using a surgical microscope.

In such surgical microscopy applications, among other types of microscopy, certain overlay content may be generated and made viewable to a user of the microscope in the field of view of the microscope. The overlay content may be synthetic content, such a digitally generated annotations, information fields, various displays and indicators, etc. The overlay content may include, or may be based on image or analytic content, such as measurements or characterizations of objects in the field of view. For example, during vitreoretinal surgery, optical coherence tomography (OCT) images and related information may be generated as overlay content, such as for viewing tissue layers in depth that are not visible with optical microscopy that OCT can make visible.

This overlay content may be generated using a suitable controller, for example, at a display, while the light from the display may then be combined with the light from the unaltered field of view of the microscope to superimpose the overlay content onto the field of view. For example, the superimposed image with the overlay content may be provided at an ocular of the surgical microscope during the ophthalmic surgery to provide image-based surgery assistance to the surgeon operating the surgical microscope.

The optical methods for enabling the display of such overlay content involve coupling, or superimposing, two optical paths onto a third optical path with certain features and properties. For instance, it may be highly desirable that all three optical paths are coaxially aligned to a common optical axis or axes. The two optical paths should be separable from each other in order to perform desired processing to generate the overlay content without interference. It would be of great advantage if the relative optical throughput (or splitting ratio) among the three optical paths could be freely defined. Furthermore, such an optical coupling should be performed in a compact volume, such that the physical space for the coupling of the optical paths is minimized, for example, in order to maintain compact dimensions of a microscope incorporating the optical coupling. Finally, the solution for optical coupling should be cost-effective to enable successful economics of any marketable product.

Conventional solutions to this problem of optical coupling have involved beam splitters with additional elements for separating beams, such as a polarizer filter, which may limit the splitting ratio to a fixed 50%/50% ratio. Other solutions may use a stack of simple beam splitters, which allows for coaxial alignment and a variable splitting ration, but at the cost of additional space and components, which may undesirably add physical space and cost. Solutions that split the optical paths into non-coaxial beams may involve constant adjustment for parallax induced misalignment of the overlay content, which is disadvantageous. Such conventional beam splitter solutions do not overcome all the disadvantages in terms of light throughput, physical dimensions, flexibility of the splitting ratio, or cost-effectiveness.

As will be described in further detail, a multi-beam splitter is disclosed that enables coaxial optical coupling for overlay content display in a microscope. The multi-beam splitter disclosed herein may enable any desired definition of the splitting ratio between the optical paths. The multi-beam splitter disclosed herein is a compact, singular optical component that minimizes physical space to enable compact designs of optical instruments in which the multi-beam splitter is incorporated. The multi-beam splitter disclosed herein allows the realization of the functionality described above using a very small footprint and a small overall stack height, which is important for mechanical compatibility with microscopes as well as minimal microscope stack height impact for optimal usability and acceptance of the solution by surgeons. The multi-beam splitter disclosed herein is also cost-effective compared to other solutions.

Referring now to the drawings, FIG. 1 is depiction of a multi-beam splitting instrument 100-1 for multi-beam splitting using spatial beam separation, as described herein. Instrument 100-1 is not drawn to scale or perspective but is a schematic representation. Instrument 100-1 may be used during ophthalmic surgery with a surgical microscope to view and analyze a human eye 102 of a patient. As shown, instrument 100-1 includes optical functionality for generating and displaying overlay content using a multi-beam splitter 128, a display 104, a sensor 106, and an ocular 126. It is noted that instrument 100-1 may be implemented with different elements in various implementations.

As shown in FIG. 1, instrument 100-1 is depicted in schematic form to illustrate optical functionality, as indicated. It will be understood that instrument 100-1 may include various other electronic and mechanical components, in different implementations. Specifically, a first beam (shown as both 110 and 112 in FIG. 1 for descriptive clarity of different optical paths) may be emitted from eye 102 in order to visualize eye 102. The first beam may be generated by a light source (not shown) that reflects light from eye 102. The first beam may accordingly arrive at multi-beam splitter 128 from eye 102, where multi-beam splitter may split the first beam into a first partial beam 112 that is transmitted by multi-beam splitter 128, and a second partial beam 110 that is reflected by multi-beam splitter 128. First partial beam 112 is transmitted by multi-beam splitter 128 towards ocular 126, which may be used for viewing by the user. Second partial beam 110 is reflected by multi-beam splitter 128 towards sensor 106 for capture and acquisition by sensor 106. Accordingly, the relative intensities of first partial beam 112 and second partial beam 110 after separation may be determined by properties of multi-beam splitter 128, as will be described in further detail with respect to FIG. 3A below. In various embodiments, sensor 106 may be a light-sensitive sensor for image acquisition or measurement at various wavelengths.

Concurrently, a second beam (as both 108 and 109 in FIG. 1 for descriptive clarity of different optical paths) may arrive at multi-beam splitter 128 at a second surface opposite from a first surface that receives the first beam described above. For example, the second beam may represent overlay content that is generated by display 104, as described in further detail with respect to FIG. 2 below, and is intended for superimposition with the first partial beam 112 at ocular 126. Accordingly, the second beam arriving at multi-beam splitter 128 may be split into a third partial beam 108 that is reflected by multi-beam splitter 128 and a fourth partial beam 109 (see also FIG. 3A) that is blocked at multi-beam splitter 128 and is not transmitted coaxially with second partial beam 110 towards sensor 106. Accordingly, the relative intensities of third partial beam 108 and fourth partial beam 109 after separation may be determined by properties of multi-beam splitter 128, as will be described in further detail with respect to FIG. 3A below. The arrangement and operation of multi-beam splitter 128 shown in instrument 100-1 enables the overlay content in third partial beam 108 to be generated at display 104, and superimposed with first partial beam 112 arriving at ocular 126 for viewing by a user. Simultaneously, sensor 106 receives second partial beam 110 without fourth partial beam 109 being superimposed thereon, enabling sensor 106 to detect and acquire the first beam from the eye 102.

Although instrument 100-1 is shown with a singular ocular 126, it will be understood that either a left or right ocular of a microscope may be implemented using ocular 126. In some implementations, instrument 100-1 may be duplicated for both a left ocular and a right ocular for stereoscopic displays of overlay content. It is noted that the designations of left and right, as used herein, may be arbitrary and may be interchangeable and may be specified herein for descriptive purposes of reference to FIG. 1. Various implementations and configurations of instrument 100-1 using multi-beam splitter 128 are described in U.S. Patent Applications titled "COMBINED NEAR INFRARED IMAGING AND VISIBLE IMAGING IN A COMPACT MICROSCOPE STACK" filed concurrently with the present application.

Figure 2:
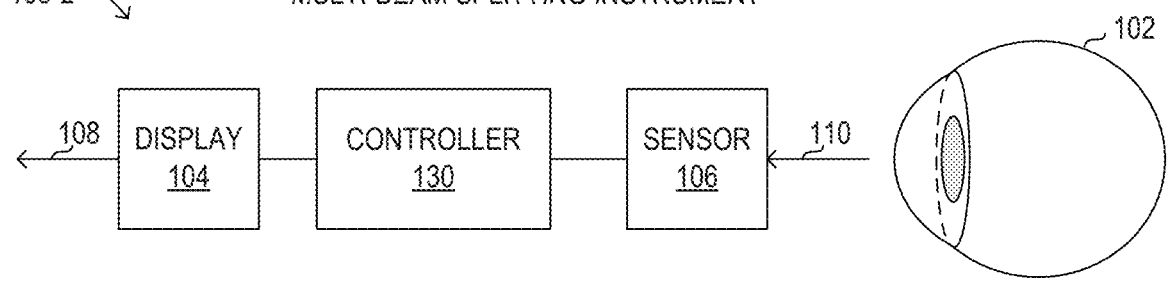
FIG. 2 is a depiction of functional elements of a multi-beam splitting instrument.

Referring now to FIG. 2, a depiction of a multi-beam splitting instrument 100-2 for multi-beam splitting using spatial beam separation, as described herein, is shown. Instrument 100-2 is not drawn to scale or perspective but is a schematic representation. As shown, instrument 100-2 includes optical and electronic functionality for generating and displaying overlay content, as described above with the optical arrangement shown in instrument 100-1. Thus FIGS. 1 and 2 both show different aspects of a multi-beam splitting instrument 100. It is noted that instrument 100-1 may be implemented with different elements in various implementations.

Specifically, in FIG. 2, the optical and electrical functionality of sensor 106 and display 104 for generating overlay content associated with eye 102 are shown. The overlay content might be an OCT image captured using near-infrared light, for example, from eye 102. The overlay image may also comprise various measurements or indications that are digitally generated from a visible light image of the eye, such as alignment features, rotational values, sizes or distances, among other measurements or indications. As shown in instrument 100-2, sensor 106 receives second partial beam 110 from eye 102, as described above with respect to instrument 100-1 in FIG. 1. Sensor 106 may acquire at least a portion of second partial beam 110 and may send corresponding image data to a controller 130 for processing. Controller 130 may process the image data and generate desired overlay content and output the overlay content to display 104. Display 104 may then generate third partial beam 108 for overlay display with first partial beam 112, as described above with respect to instrument 100-1 in FIG. 1.

Figure 5:
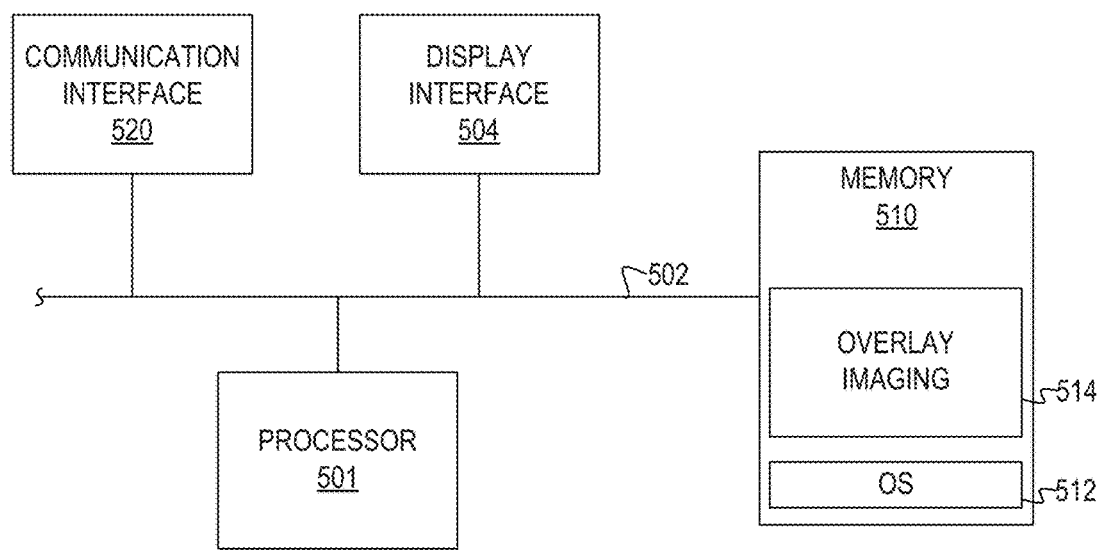
FIG. 5 is a depiction of selected elements of a controller.

In FIG. 2, controller 130 may have an electrical interface with display 104, for example, for outputting display data (see also FIG. 5). Controller 130 may output a display image to display 104 that is viewed at ocular 126. Because the electrical interface to controller 130 may support digital image data, controller 130 may perform image processing in real-time with relatively high frame refresh rates, such that a user of instrument 100 may experience substantially instantaneous feedback to user input for controlling displayed images of eye 102, as well as other operations. Display 104 may be implemented as a liquid crystal display (LCD), a light emitting diode (LED) display, such as an organic LED (OLED), a computer monitor, a television, a projector, a digital light processing (DLP) engine, or a liquid crystal on silicon (LCoS) device, among other types of display devices. Display 104 may comply with a display standard for the corresponding type of display, such as video graphics array (VGA), extended graphics array (XGA), digital visual interface (DVI), high-definition multimedia interface (HDMI), among other standards. In certain implementations, display 104 may be a miniature device that is integrated with controller 130.

Modifications, additions, or omissions may be made to multi-beam splitting instrument 100 shown in FIGS. 1 and 2 without departing from the scope of the disclosure. The components and elements of multi-beam splitting instrument 100, as described herein, may be integrated or separated according to particular applications. Multi-beam splitting instrument 100 may be implemented using more, fewer, or different components.

Figure 3A:
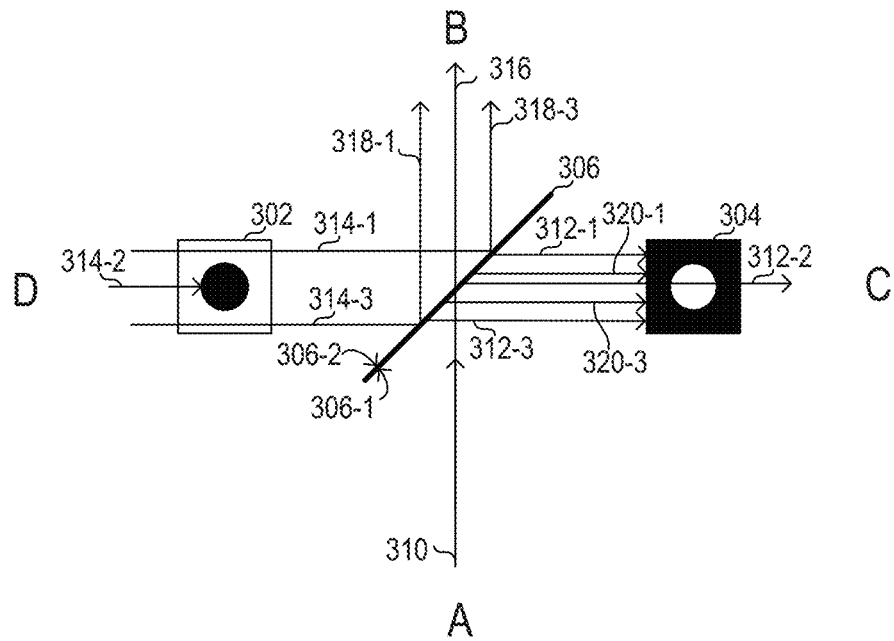
FIG. 3A is a depiction of a multi-beam splitter.

Referring now to FIG. 3A, a depiction of a multi-beam splitter 128-1 for multi-beam splitting using spatial beam separation, as described herein, is shown. Multi-beam splitter 128-1 is not drawn to scale or perspective but is a schematic representation. In FIG. 3A, further internal details describing the operation of multi-beam splitter 128 in FIG. 1 are explained. Multi-beam splitter 128-1 is shown in a generic configuration with a first source A, a second source D, a first output B, and a second output C. For example, in comparison to instrument 100-1 in FIG. 1, first source A may be an object being viewed using a microscope, such as eye 102, while first output B may be a viewing port of the microscope, such as ocular 126. Furthermore, second source D may be a source of overlay content, such as display 104, while second output C may be a sensor port for acquisition of images of the object at first source A, such as sensor 106.

In FIG. 3A, a first beam 310 arrives from first source A at a partial mirror 306 at a first surface 306-1. Because partial mirror 306 is configured to partially reflect and partially transmit incoming light at first surface 306-1, partial mirror 306 transmits a first partial beam 316 from first beam 310, and reflects a second partial beam 312 from first beam 310. Specifically, second partial beam 312 reflected from first surface 306-1 is shown comprising beams 312-1, 312-2, 312-3 over an area corresponding to an aperture filter 304 placed at second output C. Aperture filter 304 comprises an opaque field with a circular aperture having a second radius (r2) that is transparent and serves as an aperture for second partial beam 312-2 that arrives at second output C, while second partial beams 312-1, 312-2 are blocked at aperture filter 304 because they arrive at peripheral portions of aperture filter 304 outside of the aperture. Meanwhile first partial beam 316 is transmitted to first output B.

Also in FIG. 3A, a second beam 314, shown as beams 314-1, 314-2, 314-3, arrives from first source D at a spot filter 302. Spot filter 302 comprises a transparent field with a circular opaque spot having a first radius (r1) that may be comparable to second radius (r2) of aperture filter 304. In particular, first radius (r1) may be greater than or equal to second radius (r2). Accordingly, peripheral portions 314-1, 314-3 of second beam 314 arrive at a second surface 306-2 of partial mirror 306, while a central portion 314-2 is blocked at spot filter 302. Because partial mirror 306 is configured to partially reflect and partially transmit incoming light at second surface 306-2, partial mirror 306 reflects a third partial beam 318, shown as peripheral portions 318-1, 318-3 towards first output B, such that third partial beam 318 is coaxially superimposed with first partial beam 316, which enables the content from second source D to be overlaid with the content from first source A at first output B. Concurrently, second surface 306-2 also transmits a fourth partial beam 320 from second beam 314 (peripheral portions 314-1, 314-3) such that only peripheral portions of fourth partial beam 320-1, 320-3, corresponding to the transparent field of spot filter 302, are transmitted to aperture filter 304. When first radius (r1) is at least as large as, or equal to, second radius (r2), fourth partial beam 320 is accordingly blocked at aperture filter 304, because the opaque field of aperture filter 304 will spatially correspond to the transparent field of spot filter 302. Thus, peripheral portions of fourth partial beam 320-1, 320-3 are blocked by aperture filter 304, and fourth partial beam 320 is blocked by multi-beam splitter 128-1. At the aperture of aperture filter 304, only second partial beam 312-2 arrives, because a central portion of second beam 314-2 was blocked at spot filter 302, thereby preventing a central portion of fourth partial beam 320 from interfering with second partial beam 312-2.

It is noted that the absolute values of radii r1 and r2 may be chosen, relative to the size of filters 302, 304 to define a ratio of light coupled to second output C versus to first output B. Because the radii r1 and r2 can be freely chosen, this splitting ratio can be continuously varied as desired. It is further noted that in some implementations, spot filter 302 and aperture filter 304 may be exchanged in position. Spot filter 302 and aperture filter 304 may be implemented using mechanical components or opaque coatings, and the spot or aperture may be variously formed in different shapes, as an alternative to the circular shape shown in FIG. 3A and described above.

In FIG. 3A, the reflected and transmitted beam paths may have different geometries in different implementations of multi-beam splitter 128. As shown, first beam 310 along a first optical axis from first source A to first output B may be perpendicular to second beam 314 along a second optical axis from second source D to second output C, while partial mirror 306 may be oriented at 45 degrees relative to both first beam 310 along the first optical axis and second beam 314 along the second optical axis.

Figure 3B:
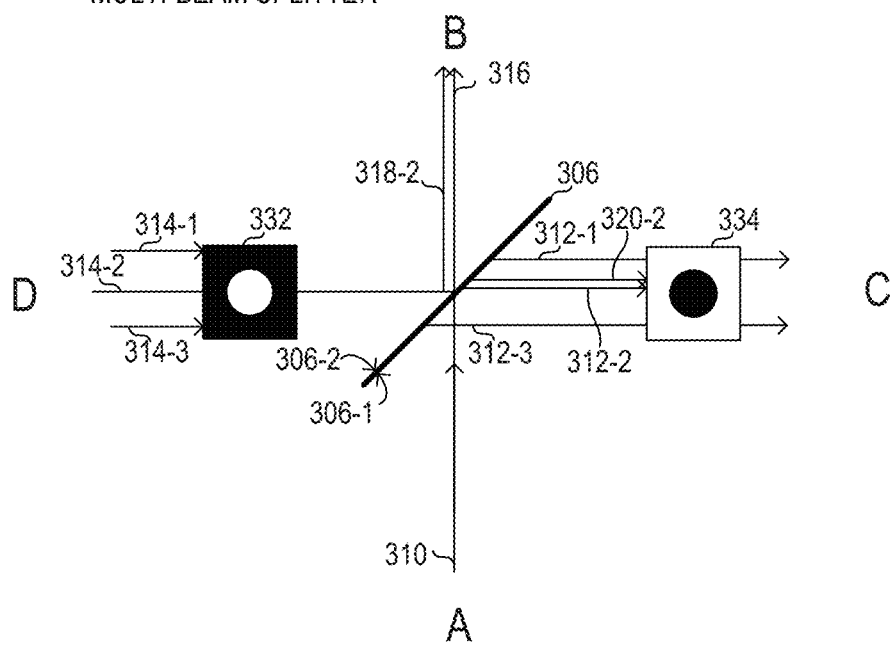
FIG. 3B is another depiction of a multi-beam splitter.

Referring now to FIG. 3B, a depiction of a multi-beam splitter 128-2 for multi-beam splitting using spatial beam separation, as described herein, is shown. Multi-beam splitter 128-2 is not drawn to scale or perspective but is a schematic representation. In FIG. 3B, an alternate implementation to multi-beam splitter 128-1 shown in FIG. 3A is depicted. Similar to FIG. 3A, multi-beam splitter 128-2 in FIG. 3B is shown in a generic configuration with first source A, second source D, first output B, and second output C.

In FIG. 3B, first beam 310 arrives from first source A at partial mirror 306 at a first surface 306-1. Because partial mirror 306 is configured to partially reflect and partially transmit incoming light at first surface 306-1, partial mirror 306 transmits a first partial beam 316 from first beam 310, and reflects a second partial beam 312 from first beam 310. Specifically, second partial beam 312 reflected from first surface 306-1 is shown comprising beams 312-1, 312-2, 312-3 over an area corresponding to a spot filter 334 placed at second output C. Spot filter 334 comprises a transparent field with a circular opaque spot having a first radius (r1) that may be comparable to second radius (r2) of an aperture filter 332. Meanwhile first partial beam 316 is transmitted to first output B.

Also in FIG. 3B, a second beam 314, shown as beams 314-1, 314-2, 314-3, arrives from first source D at aperture filter 332. Aperture filter 332 comprises an opaque field with a circular aperture having a second radius (r2) that is transparent and serves as an aperture for a central portion of second beam 314-2 that arrives at a second surface 306-2 of partial mirror 306, while remaining portions of second beam 314-1, 314-3 are blocked at aperture filter 332 because they arrive at peripheral portions of aperture filter 332 outside of the aperture. Because partial mirror 306 is configured to partially reflect and partially transmit incoming light at second surface 306-2, partial mirror 306 reflects a third partial beam 318, shown as central portion 318-2 (shown with an offset from second surface 306-2 for descriptive clarity), towards first output B, such that third partial beam 318 is coaxially superimposed with first partial beam 316, which enables the content from second source D to be overlaid with the content from first source A at first output B. Concurrently, second surface 306-2 also transmits a fourth partial beam 320 from second beam 314 (central portion 314-2) such that only a central portions of fourth partial beam 320-2, corresponding to the transparent aperture of aperture filter 332, is transmitted to spot filter 334. When second radius (r2) is at least as large as, or equal to, first radius (r1), fourth partial beam 320-2 is accordingly blocked at spot filter 334, because the opaque spot of spot filter 334 will spatially correspond to the transparent aperture of aperture filter 332. Thus, central portion of fourth partial beam 320-2 is blocked by spot filter 334, and fourth partial beam 320 is blocked by multi-beam splitter 128-2. At the transparent field of spot filter 334, peripheral portions of second partial beam 312-1, 312-3 arrive, because peripheral portions of second beam 314-1, 314-3 were blocked at aperture filter 332, thereby preventing peripheral portions of fourth partial beam 320 from interfering with second partial beam 312-1, 312-3.

As noted with FIG. 3A, the reflected and transmitted beam paths in FIG. 3B may have different geometries in different implementations of multi-beam splitter 128.

Figure 4:
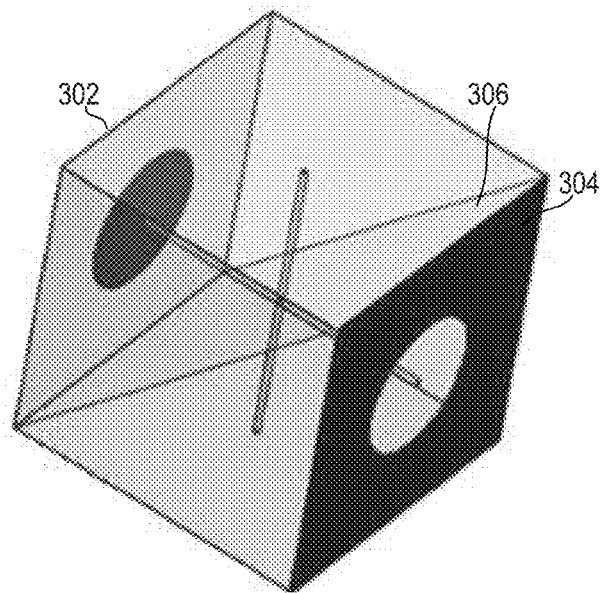
FIG. 4 is another depiction of a multi-beam splitter.

Referring now to FIG. 4, a depiction of a multi-beam splitter 400 for multi-beam splitting using spatial beam separation, as described herein, is shown. Multi-beam splitter 400 is not drawn to scale or perspective but is a schematic representation shown at a skewed angle for improved visibility. Multi-beam splitter 400 may represent a solid implementation of multi-beam splitter 128-1 in FIG. 3A. It will be understood that a corresponding solid implementation (not shown) of multi-beam splitter 128-2 in FIG. 3B may be used, with the spot filter and the aperture filters reversed, as described above. In FIG. 4, an example implementation of multi-beam splitter 400 as a cubic optical element is shown. At one face of multi-beam splitter 400, spot filter 302 is formed, while aperture filter 304 is formed on an opposing face. Also visible in FIG. 4 is partial mirror 306, which may be formed using an interface between two triangular-shaped prisms. In certain implementations, partial mirror 306 may have dichroic properties.

In summary, multi-beam splitter 128 may be used to provide parallax free overlay content in an optical system, such as a surgical microscope for ophthalmic surgery. Multi-beam splitter 128 may be implemented as a compact and relatively cost-effective optical component, that may exhibit small or limited external physical dimensions for ease of integration into a microscopy stack or other optical system.

Referring now to FIG. 5, a depiction of selected elements of controller 130, described above with respect to FIG. 2, is presented. In the implementation depicted in FIG. 5, controller 130 includes processor 501 coupled via shared bus 502 to memory media collectively identified as memory 510.

Controller 130, as depicted in FIG. 5, further includes communication interface 520 that can interface controller 130 to various external entities, such as sensor 106 and display 104, among other devices. In some implementations, communication interface 520 is operable to enable controller 130 to connect to a network (not shown in FIG. 5). In some implementations suitable for multi-beam splitting using spatial beam separation, controller 130, as depicted in FIG. 5, includes display interface 504 that connects shared bus 502, or another bus, with an output port for one or more displays, such as display 104.

In FIG. 5, memory 510 encompasses persistent and volatile media, fixed and removable media, and magnetic and semiconductor media. Memory 510 is operable to store instructions, data, or both. Memory 510 as shown includes sets or sequences of instructions, namely, an operating system 512, and an overlay imaging application 514, which may be used to perform various operations for multi-beam splitting using spatial beam separation described herein. Operating system 512 may be a UNIX or UNIX-like operating system, a Windows® family operating system, or another suitable operating system.

As disclosed herein, a multi-beam splitter enables superimposing overlay content onto an optical field of view of a microscope using a compact and flexible design that is cost-effective for many applications. The multi-beam splitter also enables capturing of the optical field of view without the overlay content.

The above disclosed subject matter is to be considered illustrative, and not restrictive, and the appended claims are intended to cover all such modifications, enhancements, and other implementations which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A multi-beam splitter, comprising:
   a beam splitter configured to receive a first beam at a first surface and a second beam at a second surface opposite the first surface, wherein the beam splitter transmits a first partial beam of the first beam and reflects a second partial beam of the first beam, and wherein the beam splitter transmits a third partial beam of the second beam and reflects a fourth partial beam of the second beam;
   a spot filter comprising an opaque spot having a first radius, the opaque spot arranged coaxially to the second beam to filter the second beam at the second surface; and
   an aperture filter comprising a transparent aperture having a second radius, the transparent aperture arranged coaxially to the second partial beam to transmit the second partial beam from the first surface,
   wherein the opaque spot of the spot filter is coaxially aligned with the transparent aperture of the aperture filter and the first radius is equal to or greater than the second radius, and wherein the third partial beam is blocked at the aperture filter.

2. The multi-beam splitter of claim 1, wherein the first beam is received along a first optical axis and the second beam is received along a second optical axis that is perpendicular to the first optical axis.

3. The multi-beam splitter of claim 2, wherein the beam splitter is oriented 45 degrees with respect to the first optical axis and the second optical axis.

4. The multi-beam splitter of claim 3, wherein the first partial beam and the fourth partial beam leave the multi-beam splitter along the first optical axis.

5. The multi-beam splitter of claim 3, wherein the second partial beam leaves the multi-beam splitter along the second optical axis.

6. An optical system, comprising:
   a first source generating a first beam;
   a second source generating a second beam;
   a multi-beam splitter enabled to receive the first beam and the second beam, and further comprising:
      a beam splitter configured to receive the first beam at a first surface and the second beam at a second surface opposite the first surface, wherein the beam splitter transmits a first partial beam of the first beam and reflects a second partial beam of the first beam, and wherein the beam splitter transmits a third partial beam of the second beam and reflects a fourth partial beam of the second beam;
      a spot filter comprising an opaque spot having a first radius, the opaque spot arranged coaxially to the second beam to filter the second beam at the second surface; and
      an aperture filter comprising a transparent aperture having a second radius, the transparent aperture arranged coaxially to the second partial beam to transmit the second partial beam from the first surface,
      wherein the opaque spot of the spot filter is coaxially aligned with the transparent aperture of the aperture filter and the first radius is equal to or greater than the second radius, and wherein the third partial beam is blocked at the aperture filter.

7. The optical system of claim 6, wherein the first beam is received along a first optical axis and the second beam is received along a second optical axis that is perpendicular to the first optical axis.

8. The optical system of claim 7, wherein the beam splitter is oriented 45 degrees with respect to the first optical axis and the second optical axis.

9. The optical system of claim 8, wherein the first partial beam and the fourth partial beam leave the multi-beam splitter along the first optical axis.

10. The optical system of claim 8, wherein the second partial beam leaves the multi-beam splitter along the second optical axis.

11. The optical system of claim 6, further comprising:
an optical sensor receiving the second partial beam from the aperture filter.

12. The optical system of claim 11, wherein the second source is a display and the second beam comprises overlay content generated by the display, and further comprising:
an ocular receiving the first partial beam and the fourth partial beam, wherein the overlay content is overlaid onto an image of the first source for viewing at the ocular.

13. The optical system of claim 12, wherein the first source is an eye of a patient subject to ophthalmic surgery.

14. The optical system of claim 12, wherein the overlay content is generated using an output from the optical sensor.

15. The optical system of claim 11, wherein the optical sensor is a camera.

16. A multi-beam splitter, comprising:
a beam splitter configured to receive a first beam at a first surface and a second beam at a second surface opposite the first surface, wherein the beam splitter transmits a first partial beam of the first beam and reflects a second partial beam of the first beam, and wherein the beam splitter transmits a third partial beam of the second beam and reflects a fourth partial beam of the second beam;
an aperture filter comprising an opaque field and a transparent aperture having a second radius, the transparent aperture arranged coaxially to the second beam to filter the second beam at the second surface;
a spot filter comprising a transparent field and an opaque spot having a first radius, the opaque spot arranged coaxially to the second partial beam to transmit the second partial beam from the first surface; and
wherein the opaque spot of the spot filter is coaxially aligned with the transparent aperture of the aperture filter and the second radius is equal to or greater than the first radius, and wherein the third partial beam is blocked at the spot filter.

17. The multi-beam splitter of claim 16, wherein the first beam is received along a first optical axis and the second beam is received along a second optical axis that is perpendicular to the first optical axis.

18. The multi-beam splitter of claim 17, wherein the beam splitter is oriented 45 degrees with respect to the first optical axis and the second optical axis.

19. The multi-beam splitter of claim 18, wherein the first partial beam and the fourth partial beam leave the multi-beam splitter along the first optical axis.

20. The multi-beam splitter of claim 18, wherein the second partial beam leaves the multi-beam splitter along the second optical axis.

21. An optical system, comprising:
a first source generating a first beam;
a second source generating a second beam;
a multi-beam splitter enabled to receive the first beam and the second beam, and further comprising:
a beam splitter configured to receive the first beam at a first surface and the second beam at a second surface opposite the first surface, wherein the beam splitter transmits a first partial beam of the first beam and reflects a second partial beam of the first beam, and wherein the beam splitter transmits a third partial beam of the second beam and reflects a fourth partial beam of the second beam;
an aperture filter comprising an opaque field and a transparent aperture having a second radius, the transparent aperture arranged coaxially to the second beam to filter the second beam at the second surface;
a spot filter comprising a transparent field and an opaque spot having a first radius, the opaque spot arranged coaxially to the second partial beam to transmit the second partial beam from the first surface; and
wherein the opaque spot of the spot filter is coaxially aligned with the transparent aperture of the aperture filter and the second radius is equal to or greater than the first radius, and wherein the third partial beam is blocked at the spot filter.

22. The optical system of claim 21, wherein the first beam is received along a first optical axis and the second beam is received along a second optical axis that is perpendicular to the first optical axis.

23. The optical system of claim 22, wherein the beam splitter is oriented 45 degrees with respect to the first optical axis and the second optical axis.

24. The optical system of claim 23, wherein the first partial beam and the fourth partial beam leave the multi-beam splitter along the first optical axis.

25. The optical system of claim 23, wherein the second partial beam leaves the multi-beam splitter along the second optical axis.

26. The optical system of claim 21, further comprising:
an optical sensor receiving the second partial beam from the spot filter.

27. The optical system of claim 26, wherein the second source is a display and the second beam comprises overlay content generated by the display, and further comprising:
an ocular receiving the first partial beam and the fourth partial beam, wherein the overlay content is overlaid onto an image of the first source for viewing at the ocular.

28. The optical system of claim 27, wherein the first source is an eye of a patient subject to ophthalmic surgery.

29. The optical system of claim 27, wherein the overlay content is generated using an output from the optical sensor.

30. The optical system of claim 26, wherein the optical sensor is a camera.

* * * * *